United States Patent
Qiu et al.

(10) Patent No.: US 9,765,378 B2
(45) Date of Patent: Sep. 19, 2017

(54) PREPARATION METHOD OF NEW RECOMBINANT ANTIBACTERIAL POLYPEPTIDE MEDICINE

(75) Inventors: Xiaoqing Qiu, Beijing (CN); Rongqi Li, Beijing (CN); Xiangli Zhang, Beijing (CN); Xiaofeng Zhang, Beijing (CN)

(73) Assignee: Creative Trio Biotech (Beijing) Co., Ltd., Beijing (CN)

( * ) Notice: Subject to any disclaimer, the term of this patent is extended or adjusted under 35 U.S.C. 154(b) by 945 days.

(21) Appl. No.: 14/001,141

(22) PCT Filed: Mar. 1, 2012

(86) PCT No.: PCT/CN2012/071825
§ 371 (c)(1),
(2), (4) Date: Jan. 6, 2014

(87) PCT Pub. No.: WO2012/119524
PCT Pub. Date: Sep. 13, 2012

(65) Prior Publication Data
US 2016/0304927 A1    Oct. 20, 2016

(30) Foreign Application Priority Data
Mar. 4, 2011    (CN) .......................... 2011 1 0052238

(51) Int. Cl.
| C12P 21/00 | (2006.01) |
| C12N 15/70 | (2006.01) |
| C12N 1/20 | (2006.01) |
| A61K 38/00 | (2006.01) |

(52) U.S. Cl.
CPC ............... *C12P 21/00* (2013.01); *C12N 1/20* (2013.01)

(58) Field of Classification Search
None
See application file for complete search history.

(56) References Cited

U.S. PATENT DOCUMENTS

| 6,995,297 B1 * | 2/2006 | Ahn | ..................... A61K 36/282 604/360 |
| 8,563,503 B2 * | 10/2013 | Qiu | ..................... C07K 14/245 435/320.1 |
| 2003/0078207 A1 * | 4/2003 | Qiu | ..................... C07K 14/245 514/2.4 |
| 2005/0271643 A1 * | 12/2005 | Sorokulova | .......... A61K 35/742 424/93.462 |
| 2012/0202734 A1 * | 8/2012 | Qiu | ..................... C07K 14/245 514/2.4 |
| 2012/0316104 A1 * | 12/2012 | Gabriel | .............. C12N 15/8281 514/2.8 |
| 2012/0328684 A1 * | 12/2012 | Shanks | .................. A01N 37/46 424/411 |
| 2014/0308345 A1 * | 10/2014 | Minatelli | ............. A61K 31/683 424/451 |
| 2015/0150794 A1 * | 6/2015 | Mudumba | ............ A61K 9/0019 514/291 |

FOREIGN PATENT DOCUMENTS

| CN | 1712534 | 12/2005 |
| CN | 101643501 | 2/2010 |
| CN | 101914603 | 12/2010 |
| EP | 1609867 | 12/2005 |
| WO | WO-2009/126890 | 10/2009 |

OTHER PUBLICATIONS

Ilic et al. (2013) Selective antimicrobial activity and mode of action of adepantins, glycine-rich peptide antibiotics based on anuran antimicrobial peptide sequences, Biochem. Biophy. Acta, vol. 1828, pp. 1004-1012.*
International Preliminary Report on Patentability and Written Opinion for PCT/CN2012/071825, dated Sep. 10, 2013, 11 pages (English translation included).
International Search Report for PCT/CN2012/071825, mailed May 31, 2012, 10 pages (English translation included).
Ruiz et al., "Cloning of the Pichia anomala SEC61 gene and its expression in a Saccharomyces cerevisiae sec61 mutant," Curr Microbiol (2003) 46(5):340-344.

* cited by examiner

*Primary Examiner* — Anand Desai
*Assistant Examiner* — Samuel Liu
(74) *Attorney, Agent, or Firm* — Morrison & Foerster LLP

(57) ABSTRACT

The invention provides a method of preparing a new recombinant antibacterial polypeptide medicine, which primarily relates to liquid culture medium formula suitable for large-scale production of the antibacterial polypeptide, as well as optimization of the enlarged culture parameters.

12 Claims, 2 Drawing Sheets

PREPARATION METHOD OF NEW RECOMBINANT ANTIBACTERIAL POLYPEPTIDE MEDICINE

CROSS-REFERENCE TO RELATED APPLICATIONS

This application is the national phase of PCT application PCT/CN2012/071825 having an international filing date of Mar. 1, 2012, which claims priority to Chinese Patent Application No. 201110052238.5, filed on Mar. 4, 2011. The contents of the above-listed applications are incorporated herein by this reference in their entireties.

FIELD OF THE INVENTION

The present invention relates to production art of antibiotic medicine, and more specifically, to preparation method of a novel recombinant antibacterial polypeptide medicine.

RELATED ART

Novel antibiotics have been studied with great efforts, among which the method of killing cells by forming ion channels on the cellular membrane of bacteria directly turns to be a promising approach. There are a lot of bacterial toxins working in said mechanism in the nature. The model example of such toxin is colicin, a bacterium toxin secreted by *Escherichia coli*. Early in 1946, H. Florey et al., the inventor of penicillin, had evaluated thoroughly about colicin on its antibacterial activity, safety and toxicology (British J. of Experimental Pathology. 1946(27), 378~390). They found that colicin is of great antibacterial activity, with very good antibacterial effect even after being diluted by millions of times. However, the antimicrobial spectrum of colicin is very specific, aiming only at *Escherichia coli* and some gram-negative bacteria with near relationships. Colicin Ia was found by Jacob et al. in 1953 with great antibacterial activity at pH 6-7. In 1978, Finkelstein et al. found an ion channel inducible colicin K that could form voltage dependent ion channels on artificial bimolecular lipid membrane, thus fundamentally explaining the antibacterial mechanism of the bacterial toxin, namely, forming fatal ion channels at the membrane of target cells. In 1996, Qiu and Finkelstein et al. revealed the transmembrane spatial structure of colicin Ia when the ion channels formed at the artificial bimolecular lipid membrane open or close, and thus provides a theoretical basis for the design and preparation of new antibiotics at a molecular level. In 2001, Qiu constructed and prepared an engineered antibacterial polypeptide medicine against drug-resistant *Staphylococcus aureus* by fusing colicin with *Staphylococcus aureus* pheromone, said polypeptide having bactericidal activity and selectivity both in vivo and in vitro. Likewise, Qiu constructed engineered antibacterial polypeptides against vancomycin-resistant *Enterococcus* and penicillin-resistant *Streptococcus pneumoniae*, said polypeptides exhibiting, in experiments both in vivo and in vitro, a specific, stable and rapid bactericidal effect against those pathogenic bacteria formidable to antibiotics now available, with pharmaceutical effect of tens to thousands times more than those of vancomycin, oxacillin, or penicillin, etc. Relevant results were published in papers such as Nature Biotechnology (21(12): 1480-85, 2003), and Antimicrobial Agents and Chemotherapy (49(3): 1184-1189, 2005), etc.

In this project, new research idea and approach is provided for the construction of engineered antibacterial polypeptides by fusing colicin with antibody mimics against pathogenic bacteria antigens, and an engineered antibacterial polypeptide, the broad-spectrum antibiotic pheromone medicine, has been successfully prepared. The inventor provides unique ideas and theoretical innovation in the field of antibacterial polypeptide drugs, with patents filed and methods established for the artificial construction of miniature antibody mimics, and relevant results published in Nature biotechnology (25(8): 921-929, 2007). Owing to its special bactericidal mechanism, the novel efficient and broad-spectrum antibiotic pheromone medicine of the project exhibits a good bactericidal effect against drug-resistant bacteria, stronger than those of antibiotics now available, such as multiple drug-resistant *Pseudomonas aeruginosa* (MDRPA), methicillin resistant *Staphylococcus aureus* (MRSA), and vancomycin resistant *enterococcus* (VRE), etc. The development and preparation of said medicine will play an important role in solving problems caused by treatment of drug-resistant bacteria as well as health care.

The broad-spectrum antibiotic pheromone medicine of the project is an entirely different material from small peptide antibiotics (e.g., human perforin and silkworm antibacterial peptide) studied home and abroad. There are several differences between the two: (1) Same as colicin, said antibacterial engineered polypeptide works in a monomer conformation, i.e., one single molecule constructing a whole working unit; whereas small peptide antibiotics work in polymer conformations, i.e., tens of molecules constructing a whole working unit. (2) Same as colicin, said antibacterial engineered polypeptide may function inside of blood circulation and in vivo; whereas small peptide antibiotics cannot. (3) Same as colicin, said antibacterial engineered polypeptide forms voltage dependent ion channels on the cellular membrane of target cells, leading to a better bactericidal mechanism and higher efficiency than the channel formed by small peptide antibiotics on the cellular membrane of target cells. According to literatures of the art searched till 2010, almost all of said small peptide antibiotics have a fatal defect in animal experiments in vivo, namely, being degraded by proteases inside of animals. Therefore, none of drugs developed from single small peptide antibiotics drug precursor had passed clinical test. However, the prototype of the new antibacterial engineered polypeptide drug developed and prepared in the project is per se a bacteriocin produced from bacteria coexisting in human and animal alimentary canals with entirely different structure and function mechanism from single small peptide. In the 8 years of tests both in vivo and in vitro, the medicine always shows great bactericidal activity, and performs good bactericidal and therapeutic effect in large animal (e.g., milk cows and goats) models either administrated by local injections or by intravenous injections. Thus, there is no limitation for the new drug of said antibacterial engineered polypeptide to be used in vivo as those for said small peptides.

It's shown by searching literature that at present, colicin, bacterial signal transduction polypeptides as well as antibody modifications are studied respectively abroad, but there is no research conducted with such research idea or technique route as in the present project, and no similar paper published. It's shown by searching at NCBI (www.ncbi.nlm.nih.gov) in June, 2010 that there were over 2600 literatures listed about colicin, over 7300 about pheromone, over 2100 about antibody reconstitution, over 3800 about immunotoxin, and over 94000 about antibiotic resistance, among which none such scientific conception, design idea or research practice as in the present project reported. In June, 2010, it's manifested in a novelty search by the novelty search workstation (No. 1) of the Ministry of Education, P.R.

China that, except for the present project reports, there was no report, both at home and abroad, on the construction of antibacterial engineered polypeptide medicine against target bacteria that utilizes colicin to bind to the target bacterial pheromone or artificial designed target bacterial antibody mimics Meanwhile, there was no report, both at home and abroad, on human or animal drugs or pesticides prepared according to construction method of the targeted antibacterial engineered polypeptide of the project.

Said broad-spectrum antibiotic pheromone medicine has been developed for animal (a drug for the treatment of bovine mastitis) and human (antibiotics) in accordance with actual demands. It's demonstrated by antibacterial tests both in vivo and in vitro that, said pheromone exhibits strong antibacterial effect, especially in vivo, which is much better than that in vitro. In May, 2010, it's proven in a safety evaluation by the Veterinary Drug Supervision & Test Center, Ministry of Agriculture, P. R. China that said medicine is non-toxic and will not cause mutation or teratogenesis. The finished medicine safety evaluation results are as follows:

① it's shown by acute toxicity test on rats and mice that said drug is non-toxic (Report No. WTPJ20100003);

② *Salmonella typhimurium* reverse mutation (Ames) turns to be negative, indicating non-mutagenicity of said drug (Report No. WTPJ20100003 (2));

③ Rat marrow osteocyte micronuclear test result is negative, which indicates there is no mutagenicity of said medicine (Report No. WTPJ20100003 (3));

④ Mice sperm malformation test result is negative, which indicates there is no teratogenesis-causing effect on mice sperm (Report No. WTPJ20100003 (4)).

⑤ the recombinant antibacterial polypeptide medicine was tested for the in vitro inhibition and bactericidal effect on bovine mastitis isolated pathogenic bacteria.

Results Show that:

A. The recombinant antibacterial polypeptide medicine has broad-spectrum antibiotic effect, as well as good inhibition and bactericidal effect on various bovine mastitis pathogenic bacteria in vitro.

B. The recombinant antibacterial polypeptide medicine (Patent Application Title: A novel antibiotic and nucleotide sequence, preparation method and application thereof, Application No. CN200910157564.5) has best inhibition and bactericidal effect against *Staphylococcus* (*Staphylococcus aureus, Staphylococcus epidermidis, Staphylococcus saprophyticus,* and *Staphylococcus sciuri*), with $MIC_{50}$ of 0.125 µg/mL, and $MBC_{50}$ of 0.25 µg/mL, which is extremely significant difference from controls of cephalothin (2 ug/ml), oxacillin (4 ug/ml), penicillin, ampicillin, lincomycin, and gentamicin (each with over 8 ug/ml). After standardization according to the medicine molecular weight, the inhibition and bactericidal effect of polypeptide (MW 70,000) against *Staphylococcus* is 2100 times as that of cephalothin (MW 523), and 5,300 times as that of oxacillin (MW 423).

C The recombinant antibacterial polypeptide medicine shows equivalent inhibition and bactericidal effect against *Streptococcus, Arcanobacterium pyogenes,* and Enterobacteriaceae (such as *Escherichia coli,* etc.), with 1.0 µg/mL of $MIC_{50}$ and 2.0 µg/mL of $MBC_{50}$ against *Streptococcus* (*Streptococcus agalactiae, Streptococcus dysgalactiae, Streptococcus uberis,* and *Streptococcus bovis*), 0.25 µg/mL of $MIC_{50}$ and 1.0 µg/mL of $MBC_{50}$ against *Arcanobacterium pyogenes,* as well as 1.0 µg/mL of $MIC_{50}$ and 1.0 µg/mL of $MBC_{50}$ against Enterobacteriaceae (such as *Escherichia coli,* etc.).

D There is no significant difference of inhibition and bactericidal effect for recombinant antibacterial polypeptide medicine between sensitive strain and the drug-resistant strain of bacteria, but the recombinant antibacterial polypeptide medicine has high-efficient inhibition and bactericidal effect against various drug-resistant *Staphylococcus, Streptococcus* and *Escherichia coli.*

In previous large animal treatment test (bovine mastitis experimental therapy), 112 was cured, with a cure rate of 95%. It's detected by the State Veterinary Drug Safety Assessment Center that, the medicine belongs to non-toxic drugs, and will not generate toxicity or harmful effect towards animals. Meanwhile, as a degradable pheromone substance, said medicine avoids drug residues of normal antibiotics after the treatment of diseases of beasts and birds. It's illustrated by a test by the Beijing Dairy Quality Supervision & Inspection Station that there is no antibiotic residue detected from the milk produced by cows treated with said medicine (Detection Report No. A2009-249).

As for the production of said recombinant antibiotic, the previous patent application (Patent Application Title: A novel antibiotic and nucleotide sequence, preparation method and application thereof, Application No. CN200910157564.5) discloses, in Example 1 of the description, an integrate preparation method of said antibacterial peptide, wherein routine culturing method was performed during the steps of expression of the recombinant protein induced by enriched bacteria after a recombinant plasmid was obtained and transformed into competent cells. During the experiment stage, there is no high requirement on production efficiency and preparation quantity. However, after the medical value of the recombinant antibacterial peptide is verified by clinical, animal experiments and safety assessment. The cost of preparation process in said patent application is too high to be used and also hardly to obtain plenty of recombinant protein expression products with high purity. Therefore, how to conduct efficient development and production in large scale is an problem which must be solved in practical application for said medicine.

SUMMARY OF THE INVENTION

Aimed at the absence of said field and the emergent demands, the invention provides preparation method of said recombinant antibacterial polypeptide.

Provided is a preparation method of the novel recombinant antibacterial polypeptide medicine, comprising the following steps:

(1) Preparing *Escherichia coli* strain comprising recombinant plasmid, and freezing for conserving, (2) Enlarging cultivation of the strain in liquid production medium, and (3) inducing the strain to express the recombinant antibacterial polypeptide and purifying the polypeptide, characterized in that, said liquid production medium comprises, in w/v, disodium hydrogen phosphate of 0.4%-0.7%, potassium dihydrogen phosphate of 0.1%-0.6%, ammonium chloride of 0.05%-0.2%, calcium chloride of 0.0005%-0.001%, magnesium sulfate of 0.5%-2.5%, peptone of 1%-3%, yeast extract powder of 0.5%-1%, glucose of 0.1%-0.5%, sodium chloride of 0.2%-0.8% and water of the rest.

Said liquid production medium comprises, in w/v %, disodium hydrogen phosphate of 0.68%, potassium dihydrogen phosphate of 0.3%, ammonium chloride of 0.1%, calcium chloride of 0.001%, magnesium sulfate of 0.02%, peptone of 2.5%, yeast extract powder of 0.75%, glucose of 0.2%, sodium chloride of 0.6%, and water of the rest.

Said enlarging cultivation comprises three stages, with parameters of 220 rpm, 37° C., and 3-8 hours in each stage.

Said inducing the strain to express the recombinant antibacterial polypeptide means treating bacteria liquid out of the step (2) as follows: stirring rate at 220 rpm, with maximum oxygen flow volume, 30° C. for 2~4 hours; 42° C. for 0.5 hours; and 37° C. for 1~2 hours; IPTG with a final concentration of 0.5 mM is added when getting 42° C.

Before said step (2), the strain is treated as follows:

(1) The strain is thawed at 4° C., recovered overnight in an LB liquid medium containing 50 μg/ml of AMP (adenosine monophosphate) at 220 rpm (revolutions per minute), 37° C., and then coated onto LB solid medium to cultivate single colonies;

(2) Single colony is picked and cultivated in 1.5 ml of LB liquid medium at 220 rpm, 37° C. for 5-8 hours, and then transferred into 100 ml of LB liquid medium to cultivate at 220 rpm, 37° C. for 5-8 hours.

The compositions and their ratios in said LB, in w/v, are sodium chloride of 1%, peptone of 1%, yeast extract of 0.5%, agar of 0.8-1%, and water of the rest.

Said *Escherichia coli* refer to engineered *Escherichia coli* BL-21 containing recombinant plasmid of pBHC-SA1, pBHC-SA2, pBHC-SA3, pBHC-SA4, pBHC-SE or pBHC-PA.

Based on a series of recombinant antibacterial polypeptide obtained by the inventor previously, a preparation method of recombinant antibiotics is provided in present invention, especially for the large-scale preparation of recombinant antibacterial polypeptide with high purity. The existing methods are not suitable for large-scale production as its unsatisfactory purity or productivity, which is a problem must to be solved during said the recombinant antibacterial polypeptides obtained previously move towards clinical application. A medium formula that is most suitable for the expression of foreign genes in *Escherichia coli* is provided in the invention via selection and optimized combination of medium components. Meanwhile, purity and productivity of the recombinant antibacterial polypeptide in large-scale production are both optimized via selection of optimum parameters for enlarged cultivation, which establishes the basis for the large-scale and industrial production of said recombinant antibacterial polypeptide.

All restriction on the availability to the public of the deposited biological materials (i.e., recombinant plasmids pBHC-SA1, pBHC-SA2, pBHC-SA3, pBHC-SA4, pBHC-SE, and pBHC-PA) will be irrevocably removed upon grant of a U.S. patent of the present application.

Figure 1:
FIG. 1 The comparison between AMP and antibacterial peptide prepared by the present method From left to right, CON: turbid after 3 hours; AMP: turbid after 4 hours; and samples prepared in Example 1: the $194^{th}$ batch of protein and the $198^{th}$ batch of protein are still clear after 27 hours.
Figure 2:
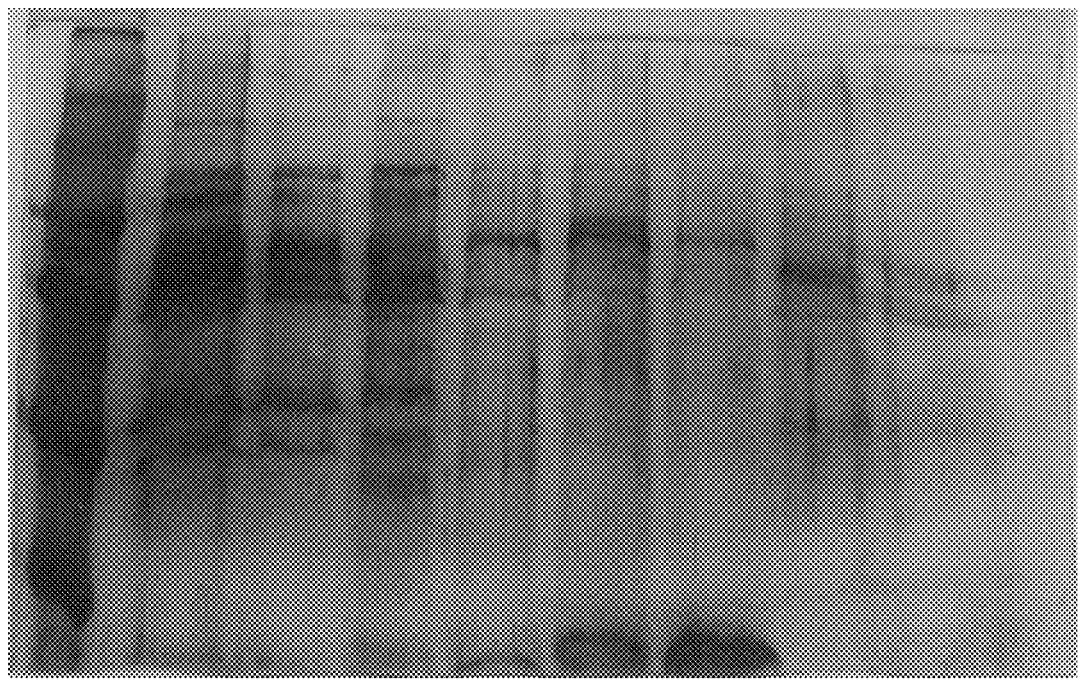
FIG. 2 purity assays of different batches of antibacterial engineered polypeptides Wherein, Band 1 is represented as the control Marker, Band 2 is represented as $120^{th}$ batch, Band 3 as $122^{nd}$ batch, Band 4 as $126^{th}$ batch, Band 5 as $246^{th}$ batch, Band 6 as $247^{th}$ batch, Band 7 as $248^{th}$ batch, Band 8 as $250^{th}$ batch, and Band 9 as $252^{nd}$ batch. Wherein, the preparation method of $120^{th}$, $122^{nd}$, and $126^{th}$ batches is routine method, while that of $246^{th}$, $247^{th}$, $249^{th}$, $250^{th}$, and $252^{nd}$ batches is the new method of the present invention.

From left to right is the productivity of shake flask, 42 L fermenter, and 200 L fermenter with continuous production of 10 batches.

EMBODIMENTS

The preparation process of the invention is exemplified with several specific recombinant antibacterial peptides as follows, but the preparation process is not limited to these specific recombinant antibacterial peptides.

Example 1 Preparation Process of Antibacterial Peptides Against *Escherichia coli, Staphylococcus Aureus, Staphylococcus Epidermidis*, and *Pseudomonas aeruginosa*

Mediums Used in the Invention:

(1) LB liquid Medium 100 mL: Sodium chloride 1 g, peptone 1 g, and yeast extract 0.5 g were added in a 250 ml flask with the addition of 100 ml water, dissolved and autoclaved at 120° C. for 8 min (2) LB Solid Medium 100 mL: Sodium chloride 0.5-1.5 g, peptone 0.5-2 g, yeast extract 0.3-1 g, and agar 0.8-3 g were added in a 250 ml flask with the addition of 100 ml water, dissolved and autoclaved at 120° C. for 8 min. The LB solid medium is used for plate culture of single colony after the strain recovery.

(3) Special Medium for Production (700 ml, 20 L, 100 L, and 200 L)

The medium solution contains, in w/v %, disodium hydrogen phosphate 0.4%-0.7%, potassium dihydrogen phosphate 0.1%-0.6%, ammonium chloride 0.05%-0.2%, calcium chloride 0.0005%-0.001%, magnesium sulfate 0.5%-2.5%, peptone 1%-3%, yeast extract powder 0.5%-1%, glucose 0.1%-0.5%, sodium chloride 0.2%-0.8% and water of the rest.

Preferred medium formula of the invention is shown in Table 1.

| NO. | Ingredients | Raw material amount in 700 ml medium (g) | Raw material amount in 20 L medium (g) | Raw material amount in 100 L medium (g) | Raw material amount in 200 L medium (g) |
|---|---|---|---|---|---|
| 1 | Disodium hydrogen phosphate | 4.76 | 136 | 680 | 1360 |
| 2 | Potassium dihydrogen phosphate | 2.1 | 60 | 300 | 600 |
| 3 | Ammonium chloride | 0.7 | 20 | 100 | 200 |

| NO. | Ingredients | Raw material amount in 700 ml medium (g) | Raw material amount in 20 L medium (g) | Raw material amount in 100 L medium (g) | Raw material amount in 200 L medium (g) |
|---|---|---|---|---|---|
| 4 | Calcium chloride | 0.007 | 0.2 | 1 | 2 |
| 5 | Magnesium sulfate | 0.14 | 4 | 20 | 40 |
| 6 | Peptone | 17.5 | 500 | 2500 | 5000 |
| 7 | Yeast extract powder | 5.25 | 150 | 750 | 1500 |
| 8 | Glucose | 1.4 | 40 | 200 | 400 |
| 9 | Sodium chloride | 4.2 | 120 | 600 | 1200 |
| 10 | Water | 700 ml | 20 L | 100 L | 200 L |

After the addition of corresponding amount of water, the medium is autoclaved at 121° C. for 8 min.
(4) Boric Acid Buffer: Boric Acid 0.04 M, NaCl 0.01M, Sodium Tetraborate 0.04M, and EDTA 2 mM
Preparation method: boric acid buffer (5 L)=solution A (1 L)+solution B(4 L)
Solution A (1 L): boric acid 12.368 g (0.2M), NaCl 2.925 g (0.05M)
Solution B (4 L): sodium tetraborate 76.27 g (0.05M)
Solution A 1 L and solution B 4 L are mixed with the addition of EDTA 2.9225 g at a final concentration of 2 mM.
Step 1 Preparing Recombinant Mutant Plasmids
Recombinant mutant plasmids pBHC-SA1, pBHC-SA2, pBHC-SA3 pBHC-SA4, pBHC-SE and pBHC-PA are prepared according to the method in Example 1 in the description of Patent with application No. CN200910157564.5 and title: "A novel antibiotic and nucleotide sequence, preparation method and application thereof".
Step 2 Transformation of Competent Cell
100 ng of the six recombinant mutant plasmids is ice-incubated with 40 ul of BL-21 engineered competent cell for 5 minutes, heat-shocked at 42° C. for 30 seconds, ice-incubated for 2 minutes, added with 160 ul of SOC medium, and shake-cultivated at 220 rpm, 37° C. for 1 hour, coated on LB medium with 1% agar and 50 ug/ml ampicillin, and cultured overnight at 37° C. Single colonies are picked and cultivated to obtain the strain, which is conserved at a low temperature.
Step 3 Recovery of the strain
1. Recovery of the Strain
The conserved strain is thawed at 4° C.; 1.5 ml of the strain is transferred into 10 ml LB medium (containing 50 µg/ml of AMP) and cultivated at 220 rpm, 37° C. for 5-8 hours.
2. Inoculation of Single Colony
The recovered bacteria solution is diluted by $10^4$ or $10^5$ times; 10 ul of the diluted bacteria solution is transferred to coat onto LB solid medium plate (containing 50 µg/ml of AMP), placed in a humid box and cultivated in incubator at 37° C. for 10-12 hours till round single colonies have grown on the surface of the medium.
3. Picking and Propagation of Bacteria
(1) Single colony with regular round shape and smooth edge is picked up by sterilized toothpick or inoculation loop from the plate, added into 1.5 ml of LB medium, and shaking cultivated at 220 rpm, 37° C. for 5-8 hours.
(2) 1.5 ml of LB bacteria solution is transferred into 100 ml of LB medium, and shaking cultivated at 220 rpm, 37° C. for 5-8 hours.

(3) Primary propagation: 100 ml of bacteria solution from the last step is added into 700 ml of special medium for production, and shaking cultivated at 220 rpm, 37° C. for 5-8 hours.
(4) Secondary propagation: 700 ml of bacteria solution from the last step is added into 6×700 ml of special medium for production, and shaking cultivated at 220 rpm, 37° C. for 5-8 hours.
(5) Third propagation: 6×700 ml of bacteria solution from the last step is added into 20 L of special medium for production, and cultivated in a fermenter with stirring rate of 220 rpm and maximum oxygen flow volume, 37° C. for 3-5 hours.
(6) Fermentation of engineered bacteria and induced expression of protein: 20 L of bacteria solution from the last step is added into 200 L of special medium for production, and cultivated in a fermenter for induced expression of protein with stirring rate of 220 rpm and maximum oxygen flow volume, at 30° C. for 2~4 hours; for 0.5 hours; and 37° C. for 1-2 hours, note that IPTG is added at 42° C. with a final concentration of 0.5 mM.
4, Centrifugation for Collecting Bacteria
6000 g culture solution is centrifuged at 4° C. for 20 min. The precipitate is collected and added into 50 mM boric acid buffer (pH9.0) to re-suspend the bacterium, which is manipulated at 4° C., note that 2 mM of PMSF is added into the boric acid buffer.
5, Thalli Fragmentation
After re-suspended in pH9.0 boric acid buffer completely, thalli was fragmented by a High Pressure Homogenizer at 500~600 bar for 7 times, with intervals of 3-5 minutes.
6, Precipitation of Thalli DNA
The fragmented bacteria solution is centrifuged at 55000 g, 4° C. for 40 min. The supernatant is added with streptomycin sulfate (16 bottles of 1 million unit streptomycin sulfate are added into every 200 ml liquid), and stirred for 1 h on a magnetic stirrer.
7, Dialysis
The bacteria solution from the last step is centrifuged at 55000 g, 4° C. for 20 min. The supernatant is placed into a dialysis bag and dialyzed for 8-12 hours in boric acid buffer, which is changed once every 4 hours.
8, Protein Medicine Purification and Obtaining of Antibacterial Engineered Polypeptide Drug
The dialyzed bacteria solution is centrifuged at 55000 g, 4° C. for 20 min. The supernatant is placed into a beaker and the protein is purified by using ion exchange method. The supernatant is uploaded onto a CM ion exchange column, washed completely, and eluted with 50 mM boric acid buffer containing 0.3M NaCl to obtain the novel antibacterial engineered polypeptide.

Example 2 Bacteria Inhibition Assay of the Polypeptide Medicine 1, 10 ml of BM medium is filled into a 100 ml conical flask and autoclaved at 121° C. for 8 min 2, the clean bench is pre-cleaned with alcohol, and then UV sterilized for 30 min 3, 3 µl of overnight cultured *Staphylococcus aureus* is filled into each 100 ml conical flasks.

4, in 100 ml conical flasks, 10 µl of sterile saline solution, 1 µl of 1 mg/ml AMP, and 125 µl of 0.8 mg/ml pBHC-SA1 polypeptide sample prepared by method in Example 1 are added and labeled respectively.

5, the mixtures are shaking cultivated at 37° C., 220 rmp.

6, they are observed at 3 h, 6 h, 9 h, 12 h and 24 h.

The blank control and AMP are turbid at 3 h, while the sample is not turbid at 9 h, which shows that the prepared sample may effectively resist *Staphylococcus aureus*, as shown in FIG. 1. Wherein, from left to right, CON: turbid after 3 hours; AMP: turbid after 4 hours; and the prepared samples of 194$^{th}$ and 198$^{th}$ batches of protein in Example 1: still clear after 27 hours.

Example 2 Comparison of the Prepared Antibacterial Peptides Between the Present Preparation Method and Routine Method Purity of different batches of the antibacterial peptide encoded by the plasmid pBHC-SA1 prepared by the present preparation method and the original method (disclosed in CN200910157564.5) in equivalent production scale are compared by electrophoresis and staining in SDS-PAGE. The result shows that, at a molecular weight of about 75000, the bands of antibacterial engineered polypeptide prepared from Example 1 at Lane 5, 6, 7, and 8 are relatively unitary, whereas mixed bands containing numerous smaller molecular weight are shown at Lane 2, 3, 4, which illustrates that purity of the polypeptide prepared by the method of the invention is significantly improved.

Example 3 Improvement of the Production Process

Figure 3:
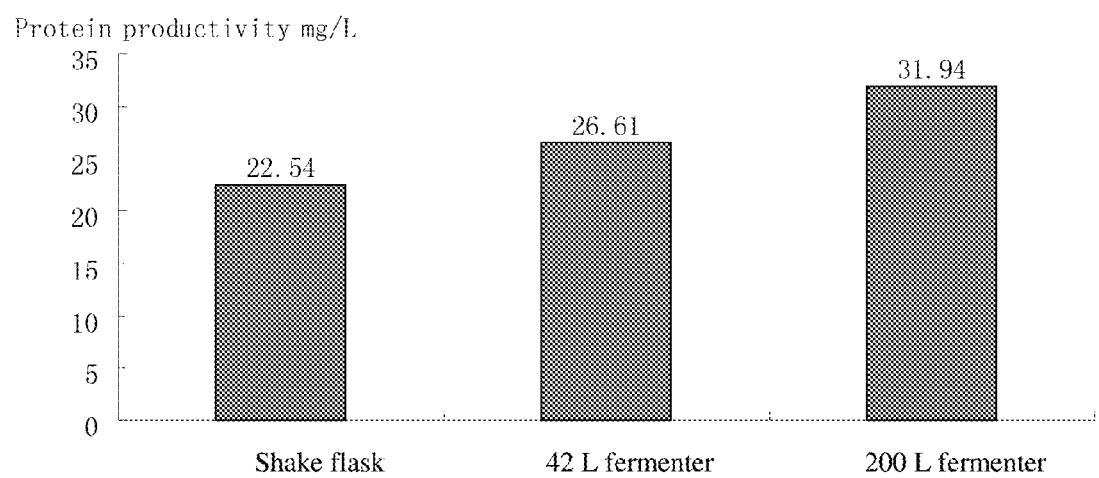
FIG. 3 productivity comparison in different scales

The production process is continuously improved and optimized, and the production scale is enlarged from a shake flask (8.4 L), to a 42 L fermenter (25 L), till the final 200 L fermenter (100 L), however the productivity is not influenced, as shown FIG. 3. Thus, it establishes the basis for the large-scale and industrial production of the antibacterial polypeptide. The yields and productivities of 10 batches of continuous production in shake flask, 42 L fermenter as well as 200 L fermenter are shown in Table 2 and FIG. 3.

TABLE 2

Yield and productivity

|  | Shake flask | 42 L fermenter | 200 L fermenter |
| --- | --- | --- | --- |
| Yield | 1893.72 | 6654.82 | 31940.00 |
| Productivity (mg/L) | 22.54 | 26.61 | 31.94 |

The invention claimed is:

1. A method of expressing a recombinant polypeptide comprising a colicin, the method comprising:
   (1) culturing an *Escherichia coli* strain in a liquid production medium, wherein the *Escherichia coli* strain comprises a recombinant plasmid encoding a recombinant polypeptide comprising colicin E1, colicin Ia, colicin Ib, colicin A or colicin B which is encoded by the polynucleotide selected from the group consisting of pBHC-SA1, pBHC-SA2, pBHC-SA3, pBHC-SA4, pBHC-SE and pBHC-PA;
   (2) inducing the *Escherichia coli* strain to express the recombinant polypeptide comprising said colicin, wherein said liquid production medium comprises water and, disodium hydrogen phosphate of 0.4%-0.7%, potassium dihydrogen phosphate of 0.1%-0.6%, ammonium chloride of 0.05%-0.2%, calcium chloride of 0.0005%-0.001%, magnesium sulfate of 0.5%-2.5%, peptone of 1%-3%, an yeast extract of about 0.5%-1%, glucose of 0.1%-0.5%, and sodium chloride of 0.2%-0.8%, wherein the percentages are weight to volume ratio (w/v, w in gram and v in milliliter).

2. The method of claim 1, wherein said liquid production medium comprises water and, disodium hydrogen phosphate of about 0.68%, potassium dihydrogen phosphate of about 0.3%, ammonium chloride of about 0.1%, calcium chloride of about 0.001%, magnesium sulfate of about 0.02%, peptone of about 2.5%, an yeast extract powder of about 0.75%, glucose of about 0.2%, and sodium chloride of about 0.6%, wherein the percentages are weight to volume ratio (w/v, w in gram and v in milliliter).

3. The method of claim 1, wherein said culturing step comprises three stages in successively increasing scale of the culture volumes from 8.4 L shake flask to a 42 L fermenter and then to final 200 L fermenter, wherein the *Escherichia coli* strain is cultured at a stirring rate of about 220 rpm (revolutions per minute), at a temperature of about 37° C., and for about 3-8 hours in each stage.

4. The method of claim 1, wherein said inducing step comprises subjecting the *Escherichia coli* culture from step (1) to the following steps:
   (i) culturing the *Escherichia coli* culture at the following conditions: stirring rate of about 220 rpm (revolutions per minute) with an optimized oxygen flow volume to allow large scale production of said polypeptide comprising said colicin, and said culturing is performed at about 30° C. for about 2-4 hours;
   (i) culturing the *Escherichia coli* culture from step (i) at about 42° C. for about 0.5 hours; and
   (iii) culturing the *Escherichia coli* culture from step (ii) at about 37° C. for about 1-2 hours, wherein IPTG is added to the *Escherichia coli* culture at step (ii) so that the final concentration of the added IPTG is about 0.5 mM.

5. The method of claim 1, wherein the *Escherichia coli* strain of step (1) is obtained as follows:
   (i) thawing a frozen stock of the *Escherichia coli* strain at about 4° C. and recovered;
   (ii) recovering the thawed *Escherichia coli* strain overnight in an LB liquid medium comprising about 50 µg/ml of AMP (adenosine monophosphate), at a stirring rate of about 220 rpm (revolutions per minute), and at a temperature of 37° C.;
   (iii) inoculating the LB liquid medium comprising the *Escherichia coli* strain onto an LB solid medium to cultivate single colonies of *Escherichia coli* strain;
   (iv) picking at least one of the cultivated single colonies and culturing the picked colonie(s) in about 1.5 ml of LB liquid medium at a stirring rate of about 220 rpm, and at a temperature of about 37° C. for about 5-8 hours; and (v) transferring the culture of step (iv) into about 100 ml of LB liquid medium and for culturing at a stirring rate of about 220 rpm, and at a temperature of about 37° C. for about 5-8 hours, wherein said LB solid medium comprises water and are sodium chloride of about 1%, peptone of about 1%, yeast extract of about 0.5%, agar of about 0.8~1%, wherein the percentages are weight to volume ratio (w/v, w in gram and v in milliliter).

6. The method of claim 1, wherein said *Escherichia coli* strain is an engineered *Escherichia coli* BL-21 strain.

7. The method of claim 1, wherein said recombinant plasmid is pBHC-SA1.

8. The method of claim 1, wherein said recombinant plasmid is pBHC-SA2.

9. The method of claim 1, wherein said recombinant plasmid is pBHC-SA3.

10. The method of claim 1, wherein said recombinant plasmid is pBHC-SA4.

11. The method of claim 1, wherein said recombinant plasmid is pBHC-SE.

12. The method of claim 1, wherein said recombinant plasmid is pBHC-PA.

* * * * *